(12) United States Patent
Tocque et al.

(10) Patent No.: US 6,372,432 B1
(45) Date of Patent: Apr. 16, 2002

(54) METHODS AND COMPOSITION FOR THE DETECTION OF PATHOLOGIC EVENTS

(75) Inventors: Bruno Tocque, Courbevoie; Laurent Bracco, Paris; Fabien Schweighoffer, Vincennes, all of (FR)

(73) Assignee: Exonhit Therapeutics SA, Paris (FR)

( * ) Notice: Subject to any disclaimer, the term of this patent is extended or adjusted under 35 U.S.C. 154(b) by 0 days.

(21) Appl. No.: 09/456,461

(22) Filed: Dec. 8, 1999

(30) Foreign Application Priority Data

Sep. 16, 1999 (FR) ............................................. 99 11563

(51) Int. Cl.$^7$ ......................... C12Q 1/68; C12N 15/74; C07H 21/04; C07H 21/02
(52) U.S. Cl. ......................... 435/6; 435/91.2; 435/471; 435/91.51; 535/23.1; 535/23.5; 535/24.33
(58) Field of Search ...................... 435/6, 91.2, 172.3, 435/320.1, 810, 91.51, 471; 436/501; 536/23.1, 24.33, 24.5, 23.3; 935/77, 78

(56) References Cited

U.S. PATENT DOCUMENTS

| | | | | |
|---|---|---|---|---|
| 4,888,278 A | * | 12/1989 | Singer et al. ................... | 435/6 |
| 5,674,682 A | * | 10/1997 | Croce et al. ................... | 435/6 |
| 5,985,549 A | * | 11/1999 | Singer et al. ................... | 435/6 |
| 6,060,240 A | * | 5/2000 | Kamb et al. ................... | 435/6 |

OTHER PUBLICATIONS

Diatchenko et al., "Suppression subtractive hybridization: a method for generating differentially regulated or tissue–specific cDNA probes and libraries," Proceedings of the National Academy of Sciences of USA 93:6025–6030 (1996).

Spilsbury et al., "Isolation of a novel macrophage–specific gene by differential cDNA analysis," *Blood* 85:1620–1629 (1995).

Tröster et al., "One gene, two transcripts; Isolation of an alternative transcript encoding for the autoantigen Ia/SS–B from a cDNA library of a patient with primary Sjögrens' syndrome" *Journal of Experimental Medicine* 180:2059–2067 (1994).

Lorson et al. A simple nucleotide in the SMN gene regulates splicing and is responsible fro spinal muscular atrophy. Proc. Natl. Acad. Sci. USA. vol. 96, pp. 6307–6311, May 1999.*

* cited by examiner

*Primary Examiner*—Stephanie Zitomer
(74) *Attorney, Agent, or Firm*—Clark & Elbing LLP; Kristina Bieker-Brady, Ph.D.

(57) ABSTRACT

The present invention concerns new compositions and methods for the detection of pathological events. It more specifically concerns methods for the detection in vitro of the presence of a pathology or a pathological event in a subject, comprising taking a sample of blood cells from the subject and determining, in this sample, the presence of blood cells presenting a physiological state characteristic of the pathology. The invention also concerns the tools, kits and compositions for the implementation of such methods, as well as their uses in the field of human and animal health, or in experimental research for example.

11 Claims, No Drawings

METHODS AND COMPOSITION FOR THE DETECTION OF PATHOLOGIC EVENTS

This application claims priority to the French application 99 11563 filed Sep. 16, 1999.

The present invention concerns new compositions and methods for the detection of pathological events. It more particularly concerns compositions and methods for the remote detection of pathological events. The invention also provides for the tools, kits and compositions for the implementation of such methods, as well as their uses in the field of human or animal health, or, for example, in experimental research.

The ageing of populations in industrialized countries has given rise to new needs in diagnostics. Diseases such as cancer or neurodegenerative disorders would be better managed to the benefit of both patients and society if diagnostic tools were available to predict the onset or progression of the disease.

Experience has shown that the earlier the diagnosis is made, the greater the chance of controlling the probable course of the disease. This has been very clearly established in the case of cancer. Early detection campaigns for breast cancer through the use of routine mammography have improved the life expectancy of these cancers. Likewise, it might be presumed that early intervention in patients who develop Alzheimer's disease would make it possible to significantly slow its progression.

The incidence of diseases such as cancer and neurodegenerative disorders increases sharply with the age of the population. It is likely that these diseases take years to develop to the point where they can be detected. It has been found, for example, that an accumulation of successive mutations in the human genome is required to initiate a cancer. Similarly, genetic studies in selected cohorts with a high incidence of Alzheimer's disease, together with genetic experiments in animals, further underscore the multifactorial nature of initiation of this disease.

These age-related diseases share some common features including:
- cellular alterations occurring in response to a disequilibrium in the environment of the affected tissues due to damage by physical, chemical or biological agents;
- the involvement of cells of the immune system.

Although alterations in the affected tissues are preferentially identified only by biopsy, it may be the case that alterations in immune cells, which reflect an ongoing disease process, can be detected far from the sites of development of these diseases, since most cells in the immune system circulate between tissues and the blood or lymph compartments.

Lymphocytic cells and macrophages are the principal mediators of the cellular immune response. Lymphocytes and macrophages are present in both tissues and blood. They are the first cells to come into contact with foreign tissues. Macrophages degrade the concerned tissues and substances. The peptides derived from the degraded proteins are then bound by the major histocompatibility system class II molecules which transport them to the macrophage surface, where the complexes are recognized by T lymphocytes. Other systems of peptide presentation and immune response activation exist and have been described notably in the case of development of cancer.

Today, diseases such as these are diagnosed after the pathology is already present. In the case of cancer, for example, the diagnosis is made on the basis of medical imaging studies and morphological diagnosis of biopsied tissues. For diseases such as Alzheimer's disease, the diagnosis is made on the basis of a body of medical findings.

Thus there is a real need for tools and methods enabling early, simple and reliable detection of the development of disease, particularly diseases related to defects in cell signalling regulatory mechanisms, especially those diseases characterized by excessive cell proliferation such as cancer, neurodegenerative disorders, stenosis, etc.

The advent of molecular biology methods combined with bio-information technologies has made it possible to construct libraries (or banks) of DNA fragments characteristic of a given pathology, enabling the detection of the presence or absence of pathological markers in a very small sample of any tissue.

The present invention now sets forth a new approach for the detection of pathologies in vitro. More specifically, the present invention describes new methods and compositions for the detection of pathological events, notably pathological genetic signatures. The invention further describes methods and compositions usable for the remote detection of pathological events, i.e. using biological materials distinct from the pathological tissues. The compositions and methods provided for by the invention now offer clinicians, biologists and industrialists new solutions for in vitro diagnosis, based on direct, rapid, sensitive and economical methods that can be automated.

More particularly, the present invention is based notably on the demonstration that it is possible to determine, from biological samples comprising circulating cells, the presence or the risk of development of a pathology. More particularly, the invention is based on the demonstration that it is possible to detect, in a biological sample comprising blood cells, the existence of a pathology, including at very early stages of initiation and development, for which all other existing diagnostics would be ineffective.

A first subject of the invention is based more specifically on a process for the detection in vitro of the presence of a pathology in a subject, comprising the taking of a sample of blood cells from the subject and the determination, in this sample, of the presence of blood cells displaying a physiological state characteristic of the disease.

In a specific embodiment, the process of the invention comprises the determination of the presence, in the sample, of blood cells presenting a protein or a protein domain characteristic of the disease. In this context, the term "presenting" refers to both the presence of this protein or protein domain inside the cell (in any cellular compartment) and its presence in the cell membrane or at the cell surface. In this embodiment, the presence of the protein (or protein domain) can be determined by means of antibodies (or fragments or derivatives of antibodies) or by any other method familiar to those skilled in the art.

In another specific embodiment, the process of the invention comprises the determination, in the sample, of the presence of blood cells presenting a genetic profile characteristic of the disease.

Even more preferably, the process of the invention comprises the determination, in the sample, of the presence of blood cells presenting alterations in gene expression characteristic of the presence of the disease.

Thus, the present invention is based firstly, on the use of blood cells in a remote test for the presence of a pathological event and, secondly, on the use of genomic methods of detection of alterations in the expression (particularly the transcription) of the genome in these cells.

In a specific variant, the present invention therefore comprises more preferably the determination, in a biological sample, of the presence of blood cells presenting transcriptional and/or post-transcriptional alterations in gene expression characteristic of the presence of a disease.

The invention is based on the demonstration that it is possible to detect a pathology in the progress of development from the genomic signatures identified in the blood cells, as pathological embryonic foci may exist in nerve tissue such as brain or spinal cord (sites of neurodegenerative diseases) or in any other tissue from which a cancer can develop, for example (breast, lung, prostate, liver, bone, etc.).

The invention demonstrates in an unexpected manner that there exist in blood cells (preferably nuclear cells such as lymphocytes, macrophages, monocytes, dendritic cells, etc.) transcriptional and post-transcriptional alterations in gene expression resulting from direct or indirect interaction(s) with the cells during initiation of the disease.

More particularly, the invention demonstrates in an unexpected manner that there exist in blood cells (preferably nuclear cells such as lymphocytes, macrophages, monocytes, dendritic cells, etc.) qualitative alterations in gene transcription following direct or indirect interaction(s) with the cells during initiation of the disease.

According to another preferred embodiment, the process of the invention comprises (i) the preparation of nucleic acids from the sample and (ii) the hybridization of the nucleic acids so prepared with at least one bank of nucleic acids characteristics of a pathological state, the hybridization profile indicating the presence, in the sample, of blood cells characteristic of the pathology.

More particularly, in one embodiment of the invention, the bank used comprises nucleic acids specific for genes whose level of expression is modified in a blood cell from a body in a pathological situation.

In another embodiment of the invention, the bank used comprises nucleic acids specific for splicing forms of genes characteristic of a blood cell from a body in a pathological situation.

The invention is based notably on an original method, the qualitative analysis of differences related to the presence of insertions or deletions (alternative splicing) in regions essential for the function of the gene products. These insertions and deletions are precisely regulated and are characteristic of physiological and pathophysiological states (especially proliferative and differentiated states) in the cells of the body. This level of regulation is modified during the onset, maintenance and development of a large number of pathologies. In a preferred embodiment, the invention is therefore also based on the application of a genomic technology designed to routinely analyze these deregulations for the purpose of developing predictive diagnostic tests. The invention thus enables the identification of the deregulated genes in circulating cells during pathological events, and the use of these qualitative genetic events in diagnostic tests for the prediction or detection of pathological events, which contribute to the overall control of health costs.

With a view to identifying the specific markers of gene expression present in the blood cells of an organism with a disease, for example at a stage too early to be diagnosed through clinical examinations or classical diagnostic tests, the present invention advantageously provides for the identification of post-transcriptional alterations. In fact, these alterations result primarily from a modification in the regulation of a key step in gene expression: splicing. Alternative splicing qualitatively modifies RNA by including or excluding exons or introns from this RNA whose presence or absence related to a given pathophysiological situation can provide the basis for a diagnosis. This diagnosis can be based on the use of PCR or hybridization to allow specific differential detection of the spliced sequence between the two situations. Alternative splicing, through the use of alternative exon(s) or by retention of intron(s) in a messenger RNA, often affects the sequence of the corresponding protein. These differences in the amino acid sequence make it possible to envision a diagnosis based on the use of antibodies that specifically recognize the alternative protein sequence.

As noted above, the process of the invention is based particularly on the use of circulating cells as biological material. More specifically, these are blood cells, preferably nuclear cells. Lymphocytes, macrophages, monocytes, dendritic cells, etc. may be cited in particular. These cells can be harvested from a subject by any method known to those skilled in the art, including cytapheresis, Ficoll gradients, preparation of peripheral blood mononuclear cells, etc. For purposes of implementation of the present invention, the different populations of blood cells can be separated from each other so that only a specific type presenting a specific genomic signature is used. However, the test set forth by the invention can also be carried out on a biological sample comprising unseparated blood cells. Furthermore, the circulating cells can also be (or comprise) tumor cells detached from the pathological tissue, for example in the case of metastatic processes. The nucleic acids can be prepared from the sample by any method familiar to those skilled in the art, including cell lysis, extraction, RNA isolation, etc. Furthermore, these nucleic acids are preferably treated prior to the hybridization step, for example to produce cDNA, to amplify these nucleic acids, to label them, etc. In this regard, the labelling can be radioactive, enzymatic, fluorescent, colorimetric or of any other type. The process of the invention typically comprises taking a biological blood sample, treating the blood cells to release the nucleic acids, amplifying the nucleic acids (and their reverse transcription, as the case may be), labelling the nucleic acids and hybridizing them on one or more banks.

The process of the invention can be used to detect the presence of a pathology (or a pathological event), i.e. the existence of cell mechanisms characteristic of a situation of initiation or development of a pathology, even if the clinical symptoms of such are not yet apparent. In this regard, the process of the invention can also enable the detection in vitro of the stage of progression of a pathology in a subject. Thus, the genetic signatures of the cells evolve according to the stage of progression of the pathology, and it is possible to detect, through the use of specific banks, the progression of a pathology. Furthermore, the process of the invention also enables the detection in vitro of the site of a pathology in a subject, i.e. the tissue in which the pathological site is present, for example.

As noted above, the process of the invention can be implemented for the detection of different types of pathologies, notably pathologies associated with deregulation of cell signalling pathways. These may be pathologies related to ageing, such as neurodegenerative disorders for example, or any other pathology involving particularly an abnormal level of cell proliferation, such as cancer, stenosis, etc.

In a specific embodiment, the invention concerns a process such as defined above for the detection in vitro of the presence, the stage of progression and/or the site of a neurodegenerative disorder.

In another specific embodiment, the invention concerns a process such as defined above for the detection in vitro of the presence, the stage of progression and/or the site of a cancerous disease. These may be different types of cancer such as, for example, solid tumors of the liver, lungs, head and neck, melanoma, liver, bladder, breast, etc.

The invention also provides for a process of detection in vitro of blood cells characteristic of a pathological state, comprising taking a sample of blood cells from a subject and determining the presence, in this sample, of blood cells presenting a genetic profile characteristic of a pathology.

As noted above, the invention is based in part on the constitution and the use of banks of nucleic acids characteristic of a pathological state. In a first embodiment, these are banks (or preparations) of nucleic acids comprising specific nucleic acids of genes whose level of expression is altered in a blood cell from an organism in a pathological situation.

In another embodiment, these are banks (or preparations) of nucleic acids comprising nucleic acids specific for splicing forms of genes, characteristic of a blood cell from an organism in a pathological situation.

The preparations and banks can be deposited on supports, refined and mixed, as described below in further detail.

The invention further describes methods for the preparation of such banks. In particular, these methods comprise (i) obtaining an initial nucleic acid preparation from a blood cell isolated from an organism presenting a pathology, (ii) obtaining a reference nucleic acid preparation from a blood cell isolated from an organism that does not present said pathology, (iii) a hybridization step between said initial preparation and the reference preparation, and recovery of the nucleic acids characteristic of the blood cell from the organism in a pathological situation.

The invention also describes processes of preparation of nucleic acid banks characteristic of a stage of progression of a pathology, comprising (i) obtaining an initial nucleic acid preparation from a blood cell isolated from an organism presenting a pathology at a defined stage of progression, (ii) obtaining a reference nucleic acid preparation from a blood cell isolated from an organism presenting said pathology at a different stage of progression, (iii) a hybridization step between said initial preparation and the reference preparation, and (iv) the recovery of the nucleic acids characteristic of the blood cell from the organism in a defined stage of progression of the pathology.

As explained below in further detail, the recovery of the clones can comprise either the recovery of non-hybridized nucleic acid clones, or the recovery, from the hybrids formed, of nucleic acid clones specific for splicing forms of genes.

The invention also concerns any kit that can be used for the implementation of a process as described above comprising a nucleic acid bank comprising nucleic acids specific for alterations in gene expression characteristic of blood cells of an organism in a pathological situation.

Identification of Specific Markers of Transcriptional and Post-transcriptional Alterations As noted above, the invention describes processes of preparation of nucleic acid banks characteristic of a stage of progression of a pathology, comprising (i) obtaining an initial nucleic acid preparation from a blood cell isolated from an organism presenting a pathology at a defined stage of progression, (ii) obtaining a reference nucleic acid preparation from a blood cell isolated from an organism presenting said pathology at a different stage of progression, (iii) a hybridization step between said initial preparation and the reference preparation, and (iv) the recovery of the nucleic acids characteristic of the blood cell from the organism in a defined stage of progression of the pathology.

The methods set forth by the invention more particularly comprise the constitution of nucleic acid clones and banks from RNA(s) extracted from different diseases, at different stages of their progression, and obtained from both pathological tissues and from blood cells whose genetic expression was affected by these tissues. These clones and banks are advantageously obtained by methods for differential analysis of gene expression. The differential signatures obtained are therefore specific to the differences between the healthy tissue and the diseased tissue on the one hand, and between the blood cells of the patient and the blood cells of the healthy control on the other hand. These signatures can therefore be expressed preferably in either the pathological samples or the control samples.

The nucleic acid populations used to obtain clones or to constitute banks are, for example, RNA (total or messenger RNA) of cells extracted from a pathological situation and RNA (total or messenger RNA) corresponding to a control situation, or nucleic acids derived from this total or messenger RNA by reverse transcription, amplification, cloning into vectors, etc. These nucleic acids can be prepared according to methods familiar to those skilled in the art. Briefly, these methods generally comprise lysis of the cells, tissue or sample, and isolation of the RNA by extraction. In particular, this can consist of a treatment with chaotropic agents such as guanidium thiocyanate (which destroys the cells and protects the RNA) followed by extraction of the RNA with solvents such as phenol or chloroform. Those skilled in the art are familiar with such methods (see Maniatis et al., Chomczynski et al., Anal. Biochem. 162 (1987) 156), which can be easily implemented by using commercially available kits such as the US73750 kit (Amersham) for total RNA. The RNA used does not have to be perfectly pure, and in particular the presence in the preparation of traces of genomic DNA or other cellular components such as protein, etc. is not a problem so long as they do not significantly affect RNA stability. Furthermore, in an optional manner, it is possible to use preparations of messenger RNA in place of total RNA preparations. The messenger RNA can be isolated either directly from the biological sample or from the total RNA by means of polyT sequences according to conventional methods. In this regard, messenger RNA can be obtained through the use of commercially available kits such as the US72700 kit (Amersham). The RNA can also be obtained directly from banks or from other samples prepared in advance and/or available in collections, and stored under suitable conditions.

The hybridization can be carried out under different conditions which can be adjusted by those skilled in the art. The hybridization preferably uses an excess of the nucleic acid population derived from the deregulated situation relative to the nucleic acid population derived from the control situation.

Using the product of the hybridization reaction, two main types of approaches can be used to isolate the clones characteristic of deregulation (pathological) according to the invention. The first, which is strictly quantitative, enables the generation of a nucleic acid preparation comprising all (or a significant part) of the clones resulting from a difference in the level of expression between the two situations. Such clones (and banks) are obtained by known subtractive hybridization methods consisting primarily of eliminating the hybrids formed during the hybridization step and keeping only non-hybridized clones characteristic of the deregulated situation relative to the chosen control situation.

In a preferred embodiment, however, a qualitative process is used to enable generation of a nucleic acid preparation comprising all (or a large part) of the clones resulting from functional gene mutations characteristic of the deregulated situation relative to the chosen control situation. More particularly, such a qualitative bank comprises not the entire group of clones whose expression is modified, but for example clones corresponding to splicing or deletion events that differ between the two situations. Considering the role of alternative splicing in cell regulatory and transformation pathways, such preparations (and banks) advantageously comprise clones having an important functional value and therefore likely to reflect the genetic modifications involved in the situation of deregulation. Such clones therefore enable the constitution of banks with greater predictive power and the generation of more representative genetic markers. Such qualitative banks can be constituted by the isolation from the hybrids formed during the hybridization step of nucleic acid regions corresponding to differential splicing or to deletions. Depending on the methods used, these regions correspond either to unpaired regions or to paired regions.

These two approaches are described below in more detail.

Production and Use of Differential Quantitative Banks

In a first embodiment, the present invention therefore makes use of a differential quantitative bank, i.e. a bank comprising nucleic acid clones corresponding to genes whose level of expression is modified in cells in the pathological situation relative to a control situation. Such banks can also be derived from differential quantitative analyses, pooling sequences whose expression is increased or decreased in cellular deregulation phenomena. The methods to establish this type of bank are familiar to those skilled in the art and can be broken down into the following categories:

High Flow Sequencing Electronic Subtraction

This process is based on the random sequencing of a certain number of cDNAs. A computer search engine can then be used to perform a subtraction between the two situations under analysis.

Serial Analysis of Gene Expression (SAGE)

This process is based on the recognition of a signature associated with each cDNA by using restriction enzymes and oligonucleotide adaptors. This label corresponds to a part of the cDNA sequence (10 nucleotides long so as to unambiguously identify the corresponding cDNA). The labels are then assembled for sequencing and analysis (Velculescu et al., Science, 1995, 270: 484–487). This approach therefore represents a short-cut to systematic sequencing.

Nucleic Acid Arrays

This method is based on the application at more or less high density of nucleic acids such as oligonucleotides, PCR fragments or cDNAs on solid supports such as membranes, glass plates or bio-chips. Messenger RNA probes from the healthy or pathological samples are then used in hybridization to identify messengers that are overexpressed or underexpressed.

Differential Display

This method makes use of an oligo-dT primer and random primers to perform PCR on cDNA populations. The PCR products are then compared on very high resolution gels. Differentially expressed fragments are then isolated and their presence confirmed by northern blot analysis prior to sequencing.

Several variants of this method have been described (Prashar and Weissman, PNAS, 1996, 93: 659–663). These variants differ in terms of the primer and restriction enzymes and adaptor used. As with the SAGE method, they make use of the 3'-ends of cDNAs. This approach is made accessible by the existence of several commercially available kits.

Subtractive Cloning

This method is based on the elimination of cDNAs that are common to the two samples under comparison. Thus, different kits in which the "tester" cDNA is hybridized with an excess of "driver" cDNA are available (Clontech). The final product consists of a pool of PCR-amplified fragments derived from differentially expressed cDNAs, which can be cloned in a suitable vector for subsequent analysis. RDA (Representational Difference Analysis) is another method based on this principle of subtraction (Lisitsyn et al., Science, 1993, 259: 946–951).

The implementation of these differential analytical methods therefore enables the generation of quantitative banks and clones, i.e. comprising all the sequences whose expression is increased or decreased in cellular deregulation phenomenon or phenomena involved in pathologies.

Production and Use of Differential Qualitative Banks

In another embodiment, the present invention advantageously uses a differential qualitative bank, i.e. a bank comprising nucleic acid clones of which at least part of the sequence corresponds to the sequence of the genes differentially spliced in the pathological cells and the control cells. This type of bank therefore comprises sequences that are differentially spliced in pathological deregulatory processes.

The use of a bank of this type is particularly advantageous. In fact, the different signalling pathways that are altered in many diseases such as cancer and neurodegenerative disorders, for example, involve genes and therefore mRNAs whose expression is regulated by alternative splicing. Furthermore, a growing number of examples furnished by the literature show that the RNA forms specifically observed in pathological states result from alternative splicing.

In relation to the originality of the invention, it should also be noted that the state of activation of the different types of cells that participate in the immune response is regulated by signalling cascades whose mediators are regulated by splicing.

Thus, Alzheimer's disease, Huntington's disease and Parkinson's disease are just some of the examples of diseases with a neurodegenerative component which have a true economic impact. Even though the description of the clinical features and the identification of several susceptibility genes have led to significant advances in our understanding of these diseases, the molecular mechanisms underlying their development are still quite obscure. The elucidation of the signalling cascades that are deregulated in these pathological states will undoubtedly lead to the discovery of targets amenable to diagnostic and therapeutic measures. The literature underscores the importance of alterations in RNA splicing processes.

Spinal muscular atrophy is one of the most common genetic diseases. Two genes, SMN1 and SMN2, encode identical proteins. Loss of the two SMN1 alleles and a splicing mutation in the SMN2 gene lead to disease development (Lorson et al. Proc. Natl. Acad. Sci. USA 1999, 96: 6307–6311).

Specific splicing mutations in the presinillin gene, PS1, have been found in the biopsy specimens of patients with Alzheimer's disease (Isoe-Wada et al. Eur. J. Neurol., 1999: 163–167)

The glutamate transport protein is of major importance in neurodegenerative diseases such as amyotrophic lateral sclerosis or epilepsy, for example. Splicing mutations in this transporter affect its function (Meyer et al. Neurosci. Lett, 1998. 241: 68–70).

Many examples of inactivation of anti-oncogene activity resulting from alternative splicing of the corresponding messengers are now known:

In small cell lung cancer, the gene encoding the p130 protein, a member of the RB (retinoblastoma protein) family, is mutated at a splicing consensus sequence. This mutation leads to the elimination of exon 2 which results in an absence of protein synthesis due to the presence of a premature stop codon. This finding was the first to highlight the importance of RB family proteins in tumorigenesis.

In head and neck cancers, one of the mechanisms of p53 inactivation involves a mutation in the splicing consensus sequence.

In other types of lung cancer, the gene encoding the p16/INK4A protein, an inhibitor of cyclin-dependent CDK4 and CDK6 kinases, is mutated at a splicing donor site. This mutation results in the production of a truncated protein with a short half-life. The p16 protein normally binds to CDK4 and CDK6, inhibiting their binding to type D cyclins and, in particular, the phosphorylation of RB, which results in an accumulation of active, hypophosphorylated forms of RB. In the absence of p16, RB is inactivated by phosphorylation. It should noted in fact that the p16 locus is particularly complex and that, apart from p16 expression, it enables p19 expression through alternative splicing. The p19 protein, which does not share any common amino acids with the p16 protein, can bind to the MDM2 proto-oncogene and block the cell cycle in the presence of p53, thereby acting as a tumor suppressor.

WT1, an anti-oncogene encoding a transcriptional repressor which, when mutated, can cause Wilms tumor, is transcribed to several messenger RNAs generated by alternative splicing. In breast cancer, the relative proportions of the different variants are modified in comparison with healthy tissue, providing diagnostic tools and clues to understanding the importance of the different WT1 functional domains in tumor progression.

This same phenomenon of modification of the proportions of different messenger RNA forms and protein isoforms occurs in the case of neurofibrin NF1 in neurofibromas.

This concept of modulation of splicing events as an indicator of tumor progression is also strengthened by the example of HDM2. In fact, five alternative splicing forms of HDM2 have been detected in ovarian and pancreatic cancer, and it is especially interesting that their expression increases with tumor stage.

LTBP, a component of the extracellular matrix of various tissues involved in TGF-β secretion and storage, is also produced in different isoforms. One such isoform, which is probably less sensitive to proteolysis, appears to modulate the biological activity of TGF-β and might be involved in different hepatic pathologies.

The cellular and humoral immune responses are under transcriptional control. The literature provides many examples of native isoforms produced by alternative splicing involved in these immune responses.

macrophage "scavenger" receptors are membrane glycoproteins required for the physiological and pathological response of these blood cells and their functions are regulated by isoforms generated by splicing (Gough et al. J.Lipid Res; 1998; 39: 531–543.)

Activation of T lymphocytes requires the functional presence of several regulatory proteins and receptors. Boriello et al. (J. Immunol. 1995; 155: 5490–5497) reported the presence of isoforms of the B7 activation cofactor, generated by alternative splicing of this gene, thus underscoring the considerable plasticity that these splicing variants confer to the immune response.

To take into account these phenomena and this complexity, and to thereby isolate signatures that are specific to a pathological state and present in blood cells, the process of the invention advantageously makes use of splicing events characteristic of situations of deregulation, as genetic markers.

To do so, the present invention uses, for example, differential qualitative nucleic acid banks produced according to "DATAS" methodology described in the unpublished international patent application PCT/FR 99/00547, incorporated in the present by reference. In particular, such banks can be prepared by hybridization between the nucleic acid population derived from cells isolated from the blood in a pathological situation, and the nucleic acid population derived from circulating cells in the control situation, and isolation, from the hybrids formed, of the nucleic acids corresponding to differential splicing.

In this approach, hybridization is preferably carried out in liquid phase. Furthermore, it can be carried out in any suitable devide such as tubes (Eppendorf tubes, for example), plates or any other suitable support commonly used in molecular biology. The hybridization is advantageously carried out in volumes of between 10 and 1000 µl, for example between 10 and 500 µl. It is understood that the device and volumes used can be easily adapted by those skilled in the art. The quantities of nucleic acids used for the hybridization are also known to those skilled in the art. In general, microgram quantities of nucleic acids suffice, for example between approximately 0.1 and 100 µg. Furthermore, it is possible to use the nucleic acids in a driver/tester ratio ranging from approximately 50 to 0.02, preferably from 40 to 0.1. Even more advantageously, this ratio is preferably close to or greater than 1,advantageously between approximately 1 and approximately 10. It is understood that this ratio can be adapted by those skilled in the art according to the conditions of the process (available quantities of nucleic acids, physiological situations, purpose, etc.). The other hybridization parameters, including time, temperature and ionic strength, can also be adapted by those skilled in the art. As a general rule, following denaturation of the tester and driver, for example by heating, the hybridization is carried out for approximately 2 to 24 hours at a temperature of approximately 37° C. (possibly submitted to temperature spikes), and in standard conditions of ionic strength, which can range from 0.1 to 5 M NaCl, for example. Ionic strength is known to be one of the factors that determines the stringency of a hybridization, especially in the case of hybridization on a solid support.

According to a specific embodiment of the invention, the hybridization is carried out in a phenol emulsion, for example according to the PERT method ("Phenol Emulsion DNA Reassociation Technique) described by Kohne D. E. et al. (Biochemistry, Vol. 16, No. 24, pp 5329–5341, 1977). The hybridization is avantageously carried out in a phenol emulsion maintained by thermocycling (temperature increase from approximately 37° C. to approximately 60/65° C.) and not by agitation, according to the method described by Miller and Riblet (NAR 23 (1995)2339).

Any other hybridization method in liquid phase, preferably in emulsion, can be used within the scope of the present invention. Furthermore, the hybridization can also be done with one of the strands immobilized on a support. Advantageously, it is the driver that is immobilized. This can be done notably thanks to biotinylated primers or by any other means of immobilization known to those skilled in the art.

Using the nucleic acid populations generated by hybridization, the genetic markers of the invention (the clones characteristic of qualitative genomic alterations) can be identified by any method familiar to those skilled in the art. In the case of RNA/DNA heteroduplex, these regions are mainly regions of unpaired RNA (RNA loops) and can be identified and cloned by separation of the heteroduplex and the single-stranded nucleic acids (excess nucleic acids which did not react), selective digestion of the double-stranded RNA (domains participating in the heteroduplex), followed by separation of the resulting single-stranded RNA and the single-stranded DNA. In the case of heterotriplex, these differential splicing regions consist mainly of regions of double-stranded DNA and can be identified and cloned by treatment with suitable enzymes such as an enzyme that digests RNA, followed by an enzyme that digests single-stranded DNA. The nucleic acids so obtained are directly in the form of double-stranded DNA and can be cloned in any suitable vector.

It is understood that other specific variants and conditions for the isolation of nucleic acids, hybridization and obtaining of qualitative clones, are indicated in the not-yet-published application No. PCT/FR99/00547, incorporated in the present by reference.

These methods enable the generation of clones and nucleic acid banks corresponding to qualitative genetic markers which allow blood cells from a healthy situation to be distinguished from those from a pathological situation. As indicated in the experimental section, these nucleic acid preparations are particularly useful markers to diagnose neurodegenerative disorders and cancers from a blood sample.

Diversity of the Banks

The aforementioned methods therefore enable the generation of groups of nucleic acid clones characteristic of the differences between a healthy and a pathological situation. Each method of preparation generates many clones which constitute banks. These banks can be used as is, deposited on supports, modified by the addition or removal of clones, or different banks can be combined or control clones added, etc.

The banks provided for by the invention can comprise 10 to 50,000 clones, more generally 10 to 10,000 clones, and even more preferably 50 to 5,000 clones. The clones are generally deposited in a well-ordered fashion on one or more supports so as to facilitate analysis of the hybridization results. The support can be composed of glass, nylon, plastic, fiber, etc. or generally be any solid support suitable for the deposit of nucleic acids. The banks can be deposited on the supports by conventional methods known to those skilled in the art, as described for example in the international application No. PCT/FR99/00547.

The banks used can comprise both the nucleic acid clones corresponding to the genes whose level of expression is altered (quantitative genetic markers) and the nucleic acid clones of which at least part of the sequence corresponds to exons or introns that are differentially spliced in a pathological and healthy situation (qualitative genetic markers). Thus, the genetic markers can be generated by different approaches, then pooled to obtain a response that is as predictive as possible.

It is also possible to pool the genetic markers specifically expressed in circulating blood cells in different pathologies within a same bank, on a same support. Hybridization of such a bank therefore makes it possible to monitor the development of several pathologies using a same blood sample.

A subject of the present invention is therefore also based on a nucleic acid preparation comprising qualitative and quantitative genetic markers characteristic of the cellular deregulation(s) present in circulating blood cells and indicative of pathologies. A specific subject concerns a bank comprising genetic markers characteristic of different situations of deregulation. Another subject of the invention is any solid support on which at least two banks of nucleic acids characteristic of two situations of deregulation have been deposited. In this regard, the invention further concerns a process of preparation of a DNA chip used to diagnose pathologies, comprising the application, on a solid support, of one or more nucleic acid preparations characteristic of situation(s) of deregulation.

Furthermore, in a preferred embodiment, use is made of nucleic acid banks refined through use by the selection of clones based on their actual involvement in different pathologies or in different stages of the same pathology. The initial banks can in fact comprise all the clones characteristic of genetic events of a situation of deregulation following onset of a pathology. Implementation of the diagnostic process set forth by the invention then makes it possible to observe that some of the clones hybridize with probes from early and intermediate stages of development of the pathology. These clones can therefore be identified as markers of early stages and can provide a very powerful diagnostic tool in advance of any other clinical criterion or any other diagnostic tool.

More specifically, the present invention now describes the identification and characterization of such clones, which can be used as genetic markers of the presence and the progression of diseases.

One of the major applications of the identification and cloning of these genetic markers concerns the evaluation of the hybridizing potential of RNA extracted from the blood cells of a given subject. This evaluation can be carried out by hybridizing a probe corresponding to the messenger RNA of the cells of this subject, with one or more banks of signatures characteristic of pathological situation(s), such as described above. This application is described in more detail below.

Methods for Analysis and Diagnosis of Signatures of Pathologies

The invention allows determination of the presence of signatures specific for different disease stages by hybridizing a sample of nucleic acids from cells present in the blood circulation, with the aforementioned genetic markers, the observed hybridization profile indicating the pathophysiological deregulation in the subject from which the blood sample was taken. To this end, the genetic markers used are preferably combined into banks so that the response can be as predictive as possible. One of the advantages of the present invention also concerns the large number of markers used, which makes the information obtained even more predictive. The predictive nature of the information is furthermore strengthened by the type of markers used and prepared.

A specific subject of the invention is based on a method of analysis of the status of blood cells, comprising at least one hybridization step between a) a sample of nucleic acids from blood cells and b) a nucleic acid bank corresponding to genetic events characteristic of deregulation(s) in cellular signalling pathways, the hybridization profile indicating the pathophysiological deregulations in the organism.

Other aspects and advantages of the present invention will emerge in the following experimental section, which should be considered illustrative and non-limiting.

Experimental Section
Example of Neurodegenerative Disorders: ALS

Animal models give access to biological samples which can be used to analyze the different steps in the development of a disease and to compare these steps with healthy controls.

Amyotrophic lateral sclerosis (ALS) is a neurodegenerative disease associated with different types of inclusions such as Lewis bodies and characterized by apoptosis of spinal and cortical motor neurons; frontal dementia sometimes occurs before the fatal outcome. Sporadic forms in which no mutations have been identified coexist alongside familial forms (FALS) associated with mutations in the SOD1 gene encoding superoxide dismutase. Transgenic mice expressing the human SOD1 gene bearing one of the mutations seen in FALS (mutation G93A) are available from Jackson Laboratory provided that a user's license is obtained from Northwestern University. The onset of the symptoms of ALS due to the G93A mutation in SOD1 does not result from a reduction in superoxide dismutase activity, but from an increase in its function which enhances its capacity to generate free radicals. This model reproduces in 120 days a disease with a fatal outcome having a symptom profile similar to the human disease. This model provides access to brain, spinal and peripheral blood samples.

Identification of Specific Splicing Forms in the ALS Model

ExonHit Therapeutics has developed an original approach of differential qualitative screening using DATAS (Differential Analysis of Transcripts Alternatively Spliced) technology. This technology is the subject of a patent application in Europe and the United States. The sequences identified by DATAS can be derived from alternative exons or from retention of introns in one of the two pathophysiological situations under comparison. The resulting data therefore characterize the modifications in the expression of RNA sequences which affect functional domains of proteins. Differential qualitative analysis is carried out on samples from transgenic animals and syngeneic controls aged 60 and 100 days. Sixty days corresponds to a stage that occurs shortly before the onset of first symptoms, but which is already characterized by changes in brain cell physiology, particularly by an alteration in mitochondrial metabolism. At 100 days, 50% of cortical and spinal motor neurons are dead and active apoptosis of neurons is triggered in parallel to activation of astrocytes.

Differential qualitative analysis is therefore carried out:
  on RNA extracted from brain and spinal cord specimens without preliminary isolation of neurons so as to take into account a maximum of alternative splicing events related to development of the disease.
  on peripheral whole blood or blood cell fractions.

The sequences identified by DATAS correspond to introns and/or exons whose differential expression via splicing between pathological situations and the healthy situation are validated by PCR.

Comparison of these sequences with data bases allows classification of the resulting information and a well-grounded choice of two sequences to be submitted to further study.

Subsequent Characterization of the Sequences Obtained

The sequences validated by PCR can be screened in complementary models involving neurodegenerative processes. For example, RNA from a model of cerebral ischemia or RNA from an animal model of a prion disease can be usefully studied to validate the selective expression of ALS markers or more generally of markers of neurodegenerative diseases.

The expression of the identified splicing forms will be sought in human samples from different pathologies with a neurodegenerative component:
  Blood samples from patients with neurodegenerative diseases such as Alzheimer's disease, Parkinson's disease, etc.

Example of Cancer: Upper Gastrointestinal Tract and Respiratory Tract Cancer

The transduction of transgenes has been the subject of a number of experimental applications in the field of experimental oncology. Thus, the dominant alleles of certain oncogenes are used to obtain transgenic mice, now the experimental model for the study of cancer.

Cancer is a heterogeneous family of diseases, each characterized by a complex group of gene mutations resulting in abnormal cell proliferation and dissemination of metastases. Although the identification of the gene mutations that induce the onset and progression of cancer now appears essential for the diagnosis and monitoring of tumor progression, it is the prospect of developing new, early diagnostic tools based on this knowledge that explains the important stake this research represents for the pharmaceutical industry. There are many genes which, when mutated, can give the cell cancerous properties. These genes play essential roles not only during development but also throughout the life of the cell. For example, they carry out functions as vital as growth, differentiation, DNA repair and cell survival. Genes which, when mutated, lead to the production of proteins which abnormally activate the cell cycle are called oncogenes. This category includes the cellular genes myc and ras, for example. In contrast, anti-oncogenes normally act to slow down the cell cycle. Inhibition of their activity makes the cell dependent solely on genes with a proliferative effect, therefore promoting tumor progression. This category includes the genes RB (retinoblastoma) and p53. Alongside the oncogenes and anti-oncogenes, the genes that modulate programmed cell death, or apoptosis, appear to be important players in oncogenesis. Similar to a process of physiological cell differentiation, programmed cell death is under genetic control. Loss of this ability to trigger terminal differentiation allowing removal of the cell places that cell in a situation of abnormal survival which can favor the emergence of a transformed clone. This is what is observed in human follicular lymphomas where the gene bcl-2 is overexpressed due to a translocation between chromosomes 14 and 18. This overexpression of an anti-apoptotic gene promotes abnormally long survival of cell populations in which other transforming mutations can accumulate. Programmed cell death, or apoptosis, is currently known to be an essential mechanism by which to eliminate cells which have become undesirable, whether due to a viral infection or because they have accumulated mutations that render them nonfunctional or hyperproliferative. The level of complexity governing cellular homeostasis results not only from the large number of players involved but also from the various roles that each can alternately play according to cell type or conditions. The p53 anti-oncogene and the cMyc proto-oncogene also play an important role in apoptosis control. Such complexity requires the use of approaches that are global enough to analyze modulations in the expression of all the involved genes, but also sufficiently specific so that the most relevant alterations in terms of diagnosis, monitoring of tumor progression or identification of new drug targets can be identified as quickly as possible.

By using different drivers of transcription (promoter regions), it is possible to preferentially obtain expression of the transgene in a specific tissue. In this manner one can establish tumor models that develop in a specific tissue environment. These different targeted tumor models suggest that it might be possible to detect specific signatures in circulating cells according to tumor location.

Liver-targeted Tumor Model

The murine hepatocarcinoma (HCC) model is linked to the restricted expression in liver of the SV40 virus early sequences encoding the large and small T antigens (Dubois, N., Bennoun, M., Allemand, I., Molina, T., Grimber, G., Daudet-Monsac, M., Abelanet, R., and Briand, P. (1991) Time course development of differentiated hepatocarcinoma and lung metastasis in transgenic mice. J. Hepatol., 13, 227–239). The transgene is under the control of the human antithrombin III promoter which drives early, continuous expression of the viral antigens. For this reason, hepatocellular proliferation undergoes a two-step perturbation. The proliferation index of the transgenic hepatocytes is proportionally higher than normal during liver development (from birth to 5 weeks), and then appreciably decreases, without however reaching the low levels characteristic of normal, quiescent liver. These transgenic mice systematically develop differentiated HCC that are fatal to all animals before 7 months. Despite an early deregulation of hepatocyte proliferation, hepatomegaly occurs only late in the course. Analysis of the preneoplastic steps preceding development of HCC has revealed the existence of an apoptotis compensating mechanism that maintains normal liver mass in this model (Allemand et al., 1995). It is noteworthy that this apoptosis stops at the very moment when the normal liver enters quiescence. Beyond this point, it appears that hepatic homeostasis is no longer controlled. A systematic study of sensitivity to apoptosis showed that the hepatocytes derived from this transgenic model had acquired resistance to cell death which was dependent on the CD95/Fas system (Rouquet N, Allemand I, Molina T, Bennoun M, Briand P and Joulin V. (1995) Fas-dependent apoptosis is impaired by SV40 T-antigen in transgenic liver. Oncogene, 11, 1061–1067 Rouquet N, Allemand I, Grimber G, Molina T, Briand P and Joulin V. (1996) Protection of hepatocytes from Fas-mediated apoptosis by a non-transforming SV40 T-antigen mutant. Cell Death & Diff., 3, 91–96) by a mechanism independent of alternative splicing of the CD95/Fas receptor. However, only a global analysis of splicing alterations can explain an alteration in this process for all the players involved in the CD95/Fas receptor signalling pathway.

This transgenic model is an ideal tool to identify 1) the modifications in gene expression accompanying preneoplastic transition to neoplasia, whether the genes are essential for transformation (oncogenes) or inhibit tumor progression (apoptotic genes); 2) circulating signatures of cancer development linked to escape of tumor cells from the tumor; 3) events of alteration of gene expression in blood cells characteristic of development of the cancer.

Identification of Specific Signatures

The differential qualitative approach is carried out using RNA extracted from liver and blood cells of normal mice and of mice that develop hepatocarcinoma (HCC) due to antithrombin III-driven expression of the SV40 T antigen. Control and transgenic animals are chosen at different ages so as to be able to study very early, preneoplastic and neoplastic stages which, in this model, are characterized in particular by an activation and then an inactivation of apoptosis required for hepatic homeostasis.

Use of the Identified Sequences

Alterations in the expression of these sequences can then be screened in human tumor biopsies so as to broaden the field of application in human therapy and diagnostics.

These cDNAs are used to monitor tumor progression in this transgenic model and in a series of transgenic murine HCC models (Bennoun M, Grimber G, Couton D, Seye A, Molina T, Briand P and Joulin V. (1998) The amino-terminal region of SV40 large T antigen is sufficient to induce hepatic tumours in mice Oncogene, 17, in press). Thus, by using specific cDNAs detected at different, very early stages in blood cells, before development of the tumor, it is possible to predict, in a mixed population of healthy and transgenic mice, which animals will develop a tumor.

Nucleotide probes or PCR primers derived from these tumor-specific cDNAs can be used to screen for the expression, in human tumor biopsies, of the identified splicing forms and/or the RNAs whose quantities are altered in this model.

Similarly, the probes identified in the blood of animals at different stages of tumor development can also be used to detect signatures common to blood samples from cancer patients.

In a strategy which uses the cDNA banks obtained according to the aforementioned processes of the invention, a total probe prepared from blood samples from cancer patients can also be used to screen for signatures common to the different banks established from murine models at different stages of tumor progression, on the one hand, and from biopsies of different human tumors on the other hand. These hybridizations are carried out according to methods familiar to those skilled in the art (in particular, consult the hybridization conditions set forth in application No. PCT/FR99/00547 included in the present as reference).

Research for Predictive Diagnosis in Man

The methods described in this section can be implemented by using either the quantitative or the qualitative analytical methods described above. Nonetheless, the invention favors the use and research of markers linked to qualitative alterations in gene expression, due to the aforementioned advantages.

The invention describes the identification and constitution of banks of signatures characteristic of the progression of a pathology, from biopsy samples. It is thus possible to establish banks of cDNA sequences representative of the course and site of these pathologies. It is therefore possible to screen blood samples for the presence of cDNA signatures identical to those present in the banks. The presence of common signatures then indicates the presence of nucleic acids with the same alterations as those found in the biopsy specimens for the suspected pathology, very probably derived from cells of the pathological tissues.

This screening is based in particular on the construction of probes from blood cells and the hybridization of these probes on filters bearing different markers specific to such and such a pathology.

The invention describes the possibility of identifying alterations in gene expression in blood cells, and this using experimental models that mimic all or part of a human pathology (eg., murine ALS model or hepatic tumor model).

The use of nucleic acid probes derived from blood cells of patients with or without the screened pathology (neurodegenerative disease, cancer, etc.) enables to screen for the existence of signatures that are present in the experimental predictive banks created from experimental disease models. The presence of common signatures constitutes a diagnosis that the individual being tested is at risk for developing such a pathology.

The invention also makes it possible to proceed in the following manner:

Blood samples from patients with or without a disease being screened are pooled in order to constitute a stock of RNA representing both healthy and pathological states.

This RNA is subjected to differential analyses according to the methods set forth in the invention and cDNA banks characteristic of pathological and healthy states are created.

These cDNA banks are then validated by hybridization with probes prepared from individual blood samples from patients or healthy subjects.

The banks thus validated are then analyzed through the use of probes prepared from blood samples from a large population of subjects who consult a doctor for routine tests. These banks constitute a diagnostic tool specific to the invention. For example, a patient undergoing routine breast cancer screening by mammography can have a small blood sample taken. A nucleic acid probe prepared from such a sample then makes it possible to detect very early signs indicative of development of a cancer, even in the absence of positive radiographic findings.

The invention can be used in the form of a biochip. The biochip makes use of the properties of hybridization in which two so-called complementary strands of DNA bind to each other in a highly specific manner. The invention can also be used by specifically seeking one or more DNA markers for the pathology by using a DNA amplification method with oligonucleotide primers specific for the desired DNA.

What is claimed is:

1. A process for the detection in vitro of a cancer or neurodegenerative disease in a subject, comprising (i) taking a sample of blood cells from the subject, wherein said blood cells comprise lymphocytes, macrophages, monocytes or dendritic cells, (ii) preparing nucleic acids from the sample and (iii) hybridizing all or part of the nucleic acids so prepared with at least one nucleic acid library in order to obtain a hybridization profile, wherein the nucleic acid library comprises a plurality of different nucleic acid molecules specific for splicing forms of genes wherein the splicing forms are characteristic of a cancer or neurodegenerative disease, the hybridization profile indicating the presence of blood cells in the sample characteristic of a cancer or neurodegenerative disease, thereby detecting the presence of a cancer or neurodegenerative disease in the subject.

2. The process according to claim 1, wherein said at least one library is deposited on a support.

3. The process according to claim 1, wherein the nucleic acids prepared from the sample are total or messenger RNA, or cDNA derived therefrom.

4. The process according to claim 3, wherein the nucleic acids are labelled.

5. The process according to claim 1, wherein the splicing forms are characteristic of the stage of progression of a cancer or neurodegenerative disease in a subject.

6. The process according to claim 1, wherein the splicing forms are characteristic of the site of a cancer or neurodegenerative disease in a subject.

7. The process according to claim 1, wherein the splicing forms are characteristic of the presence, the stage of progression or the site of amyotrophic lateral sclerosis in a subject.

8. The process according to claim 1, wherein the splicing forms are characteristic of the presence, the stage of progression or the site of a gastrointestinal or respiratory cancer in a subject.

9. A process for the detection in vitro of blood cells characteristic of a cancer or neurodegenerative disease, comprising taking a sample of blood cells from a subject and determining, in the sample, the presence of blood cells presenting a genetic profile characteristic of a cancer or neurodegenerative disease, wherein determining the presence of said blood cells comprises (i) extracting nucleic acids from the sample, (ii) hybridizing the nucleic acids to a nucleic acid library to obtain a hybridization profile, wherein the nucleic acid library comprises, deposited on a support, a plurality of different nucleic acid molecules specific for splicing forms of genes whose splicing is modified in a blood cell in a subject with cancer or neurodegenerative disease, the hybridization profile indicating the presence of a genetic profile characteristic of a cancer or neurodegenerative disease in said blood cells.

10. A kit usable for the implementation of a process according to claim 1, comprising a nucleic acid library, wherein the library comprises, deposited on a support, a plurality of different nucleic acid molecules specific for splicing forms of genes of blood cells from an organism with a cancer or neurodegenerative disease.

11. The process according to claim 1, wherein the at least one nucleic acid library is obtained by (i) obtaining an initial nucleic acid preparaton from a blood cell isolated from an organism presenting a cancer or neurodegenerative disease, (ii) obtaining a nucleic acid reference preparation from a blood cell isolated from an organism not presenting a cancer or neurodegenerative disease, (iii) hybridizing said first preparation and the reference preparation, and (iv) recovering nucleic acids from the hybridization mixture which are characteristic of the blood cell from the organism presenting a cancer or neurodegenerative disease.

* * * * *